United States Patent [19]

Shah et al.

[11] Patent Number: 5,009,996

[45] Date of Patent: * Apr. 23, 1991

[54] TWO SITE CROSS-REACTION IMMUNOMETRIC SANDWICH ASSAY METHOD

[75] Inventors: Vipin D. Shah, Saratoga, Calif.; Padmaker V. Kulkarni, Dallas, Tex.; Quirinus R. Miranda, San Jose, Calif.

[73] Assignee: International Immunoassay Laboratories, Inc., Santa Clara, Calif.

[ * ] Notice: The portion of the term of this patent subsequent to Apr. 23, 2008 has been disclaimed.

[21] Appl. No.: 537,947

[22] Filed: Sep. 30, 1983

Related U.S. Application Data

[63] Continuation of Ser. No. 165,001, Jun. 30, 1980, abandoned.

[51] Int. Cl.$^5$ .................. G01N 33/53; C12Q 1/50
[52] U.S. Cl. ............................ 435/7; 435/17; 435/805; 435/810; 436/518; 436/538; 436/539; 436/540; 436/542; 436/547
[58] Field of Search ................. 435/4, 7, 17, 805, 810; 436/518, 547, 538, 539, 540, 541, 542

[56] References Cited

U.S. PATENT DOCUMENTS

| | | | |
|---|---|---|---|
| Re. 29,169 | 4/1977 | Schuurs et al. | 435/7 |
| 3,932,221 | 1/1976 | Pfleiderer | 435/7 |
| 3,994,783 | 11/1976 | Rao | 435/17 |
| 4,012,285 | 3/1977 | Pfleiderer | 435/7 |
| 4,046,634 | 9/1977 | Mercer | 435/4 |
| 4,048,298 | 9/1977 | Liswender | 424/1.5 |
| 4,067,775 | 1/1978 | Wurzburg | 435/7 |
| 4,092,408 | 5/1978 | Litt | 424/1 |
| 4,105,499 | 8/1978 | Kiyasu | 435/17 |
| 4,224,406 | 10/1980 | Gomez et al. | 435/7 |
| 4,237,219 | 12/1980 | Roberts | 435/7 |
| 4,243,749 | 1/1981 | Sadeh et al. | 435/7 |
| 4,244,940 | 1/1981 | Jeong et al. | 424/1 |
| 4,260,678 | 4/1981 | Lepp | 435/7 |
| 4,267,271 | 5/1981 | Roberts | 435/7 |
| 4,298,592 | 11/1981 | Lin | 435/7 |
| 4,332,783 | 6/1982 | Pernice et al. | 435/7 |
| 4,353,982 | 10/1982 | Gomez et al. | 435/7 |

OTHER PUBLICATIONS

Roberts et al, Clin. Chim. Acta, 83:141–149 (1978).
Homburger, H. A. et al, "Creatine Kinase Radioimmunoassay and Isoenzyme Electrophoresis Compared in the Diagnosis of Acute Myocardial Infarction", *Clin. Chem.*, 26/7, 861–866 (1980).
Fiolet, J. W. et al, "Determination of Creatine Kinase Isoenzyme MB (CK-MB): Comparison of Methods and Clinical Evaluation", *Clinica Chimica Acta*, 80 (1977) 23–35, Elseview/North Holland Biomedical Press.
Roberts, R. et al, "Detection of Acute Myocardial Infarction by Radioimmunoassay for Creatine Kinase MB", *The Lancet*, vol. II, No. 8033, 319–321.
Heal, A. et al, "Clinical Evaluation of a CK-B Radioimmunoassay for the Detection of Myocardial Infarction", *The Ligand Quarterly*, 5/2, 1982, pp. 35–39.

(List continued on next page.)

Primary Examiner—Esther L. Kepplinger
Assistant Examiner—Carol A. Spiegel
Attorney, Agent, or Firm—Browdy and Neimark

[57] ABSTRACT

A two site cross-reaction immunometric sandwich assay method for the detection and measurement of an analyte, such as creatine phospho-kinase-MB, in serum comprising the selection of two different antibodies each of which is specific to a different analyte but each of which will cross-react with the analyte of interest. The first antibody is reacted with the unknown sample utilizing a solid-phase to bind the first antibody. Separation of the solid and liquid portions of the first reaction is accomplished and the solid portion thereof is reacted with the second antibody which is tagged. The solid portion and liquid portion of the second reaction are separated and the solid portion is tested for the tag as an indication of the presence of said analyte. With particular reference to testiong for creatine phospho-kinase-MB in human serum, the cross-reacting antibodies utilized are antibody to creatine phospho-kinase-BB and creatine phospho-kinase-MM.

11 Claims, 2 Drawing Sheets

OTHER PUBLICATIONS

Woodshead, J. S. et al., "The Immunoradiometric Assay and Related Techniques", *Br. Med. Bull.*, 30/1, 1974, pp. 44–49.

DePuey, E. G. et al, "Clinical Utility of a Two-Site Immunoradiometric Assay for Ceratine Kinase-MB in the Detection of Perioperative Myocardial Infarction", *J. of Nuclear Medicine*, 24/8 (1983) pp. 703–709.

Witherspoon, L. R., et al, "Two Radioimmunoassays Compared with Isoenzyme Electrophoersis for the Detection of Serum Creatine Kinase-MB in Acute Myocardial Infarction", *J. of Nuclear Medicine*, 23/2 (1982) pp. 136–142.

*Advances in Protein Chemistry*, edited by Anson, M. L. et al, vol. 1, Academic Press, Inc., New York, 1944, pp. 70–95.

Thaler, M. S. et al, *Medical Immunology*, pp. 6–8, J. B. Lippincott Company, Philadelphia-Toronto, 1977.

Boyd, W. C. *Introduction to Immunochemical Specificity*, 1965, pp. 1–7, Interscience Publishers.

Richards, F. F. et al, "On the Specificity of Antibodies", *Science*, vol. 187, 17, pp. 130–136 (1978).

Cunningham, A. J., "Understanding Immunology", Academic Press, New York, 1978, 9–15 and 18–27.

Paul, W. E., "Fundamental Immunology", Raven Press, New York, (1984) pp. 614–631 and 642–644.

Goodman, J. W., "Antigenic Determinants and Antibody Combining Sites", in Sela, M., ed., The Antigens, vol. III, Academic Press, New York, 1975, pp. 128–183.

Morgan, F. J. et al, "Nature of the Subunits of Human Chorionic Gonadotropin", *Endocrinology*, 88, 1971, pp. 1045–1053.

Vaitukaitis, J. B., et al, "A Method for Producing Specific Antisera with Small Doses of Immunogen", *J. Clin. Endocr.*, 33, 988, 1971, pp. 988–991.

"Isozymes: Current Topics in Biological and Medical Research," vol. 1, edited by M. C. Rattazzi et al, Alan R. Liss, Inc., New York (1977) at pp. 20–78.

Moss, D. W., "Isoenzyme Analysis", The Chemical Society, London, 1979, Chapter 1, pp. 1–36.

Lequin, R. M. et al, "Immunochemical Characterization of Antisera to Human Luteinizing Hormone and Its Subunits", *Horm. Metab. Res., Suppl. Ser.*, vol. 5, (Radioimmunoassay: Methodol. Appl. Physiol. Clin. Stud.), pp. 49–57, 1974, at p. 50.

Addison, G. M. et al, "The Immunoradiometric Assay", in Radioimmunoassay Methods: European Workshop on Radioimmunoassay Methods; Sep. 15–17, 1970, Edinburgh, Kirkham, K. E. et al editors, Churchill Livingston, Edinburgh and London 1971, pp. 447–488.

O'Riordan, J. L. H. et al, "Localisation of Antigenic Sites, in Parathyroid Hormone", in Endocrinology (Ed. Taylor, S.) Heinemann Medical, London, 1972, pp. 486–392.

Lang, H. et al., "Creatine Kinase, an Enzyme of Many Forms", *Clin. Chem.*, 28/7:1439–1447 (1982).

Willerson, J. T. et al, "Radioimmunoassay of Creatine Kinase-B Isoenzyme in Human Sera: Results in Patients with Acute Myocardial Infarction", *Proc. Natl. Acad. Sci. U.S.A.*, 74:1711 (1977).

Zweig, M. H. et al, "Radioimmunossay of Creatine Kinase in Human Serum. Isoenzyme BB", *Clin. Chem.*, 24:422 (1978).

Urdal, P. et al, "Sensitive and Specific Radioimmunoassay for Creatine Kinase BB Isoenzyme in Serum, with Use of an Autoantibody", *Clin. Chem.* 27:83–87 (1981).

"Alternative Immunoassays,", edited by W. P. Collins, John Wiley & Sons, Chichester, 1985, pp. 23–25.

Barrett, J. T., "Textbook of Immunologies", C. V. Mosby Company, New York (1983) p. 42.

Pudek, M. R. et al, "Falsely Negative Laboratory Diagnosis for Myocardial Infarction Owing to Concurrent Presence of Macro Creatine Kinase and Macro Lactate Dehydrogenase", *Clin. Chem.*, 28/12, 2434–2437 (1982).

Yasimeh, W. G. et al, "Chromatographic Behavior of Immunoglobulin-Bound Creatine Kinase on DEAE-Sephadex A-50", *Clin. Chim. Acta*, 144, 29–37 (1984).

Burger, A. et al, "Die Heterogenitat der Kreatin Kinase," *Biochem. Z.*, 339:305–314 (1964).

Roberts, R. et al, "Specificity of Elevated Serum MB Creatine Phosphokinase Activity in the Diagnosis of Acute Myocardial Infarction", *Am. J. Cardiol.*, 36:433–437 (1975).

Galen, R. S. et al, "Diagnosis of Acute Myocardial Infarction Relative Efficiency of Serum Enzyme and Isoenzyme Measurements", *J. Am. Med. Assn.*, 232:145 (1975).

(List continued on next page.)

OTHER PUBLICATIONS

Roe, C. R. et al, "Combined Isoenzyme Analysis in the Diagnosis of Myocardial Injury: Application of Electrophoretic Methods for the Detection and Quantitation of the Creatine Phosphokinase MB Isoenzyme", *J. Lab. Clin. Med.*, 80:577–590.

Klein, M. S. et al, "Serum Creatine Phosphokinase (CPK) Isoenzymes Following Intramuscular Injections, Surgery, and Myocardial Infarction, Experimental and Clinical Studies", *Cardiovasc. Res.*, 7:412 (1973).

Roberts, R. et al, Quantification of Serum Creatine Phosphokinase Isoenzyme Activity", *Am. J. Cardiol.*, 33:650–654 (1974).

Mercer, D. W., "Separation of Tissue and Serum Creatine Kinase Isoenzymes by Ion-Exchange Column Chromatography", *Clin. Chem.*, 20:36–40 (1974).

Witteveen, S. A. G. J. et al, "Kinetic Properties of the Isoenzymes of Human Creatine Phosphokinase", *Proc. Natl. Acad. Sci. U.S.A.*, 71:1384–1387 (1974).

Rao, P. S. et al, "A New Manual and Automated Method of Determining Activity of Creatine Kinase Isoenzyme MB, by Use of Dithiothreatol", *Clin. Chem.*, 21:1612–1618 (1975).

Roberts, R. et al, "Radioimmunoassay for Creatine-Kinase Isoenzymes", *Science*, 855–857 (1976).

Jockers-Wretou, E. et al, "Quantitation of Creatine Kinase Isoenzymes in Human Tissues and Sera by an Immunological Method", *Clin. Chim. Acta* 58:223–232 (1975).

D'Souza, J. P. et al, "The Significance of the MB Isoenzyme in Patients with Acute Cardiovascular Disease with a Normal or Borderline Total CPK Activity", *Clin. Biochem.*, 11/5:201–209 (1978).

Mercer, D. W., "Frequent Appearance of Creatine-Kinase Isoenzyme BB in Sera of Critical-Care Patients", *Clin. Chem.*, 23:611 (1977).

*Clin. Chem.* (1979) 25, 6, pp. 1025, 1027, 1028, 1030.

*Clin. Chem.* 26, 7, (1980), pp. 914, 917, 921 and 922.

*Clin. Chem.* 27, 6 (1981) pp. 1009–1013, 1024–1030, 1053.

*Clin. Chem.* 28, 7 (1982) pp. 1564–1566, 1615–1618.

Shell, W. E. et al, "Radioimmunoassay of Creatine Kinase" in Clinical Nuclear Cardiology, edited by Berman, D. S. et al, Grune & Stratton, New York, 1981, pp. 462–478.

Schillizzi, W. et al, "Radioimmunoassay to Differentially Assay Plasma MB and BB CK" in 55th Scientific Sessions of The American Heart Association, Am. Heart Assoc. Monogr., 0 (91) 1982, II-183.

Al-Sheikh W. et al, "Evaluation of an Immunoradiometric Assay Specific for the CK-MB Isoenzyme for Detection of Acute Myocardial Infarction", *Am. J. Cardiol.* 54:269–273 (1984).

Linke, E. G. et al, "Four CK-MB Methods—A Clinical Evaluation for Detection of Acute Myocardial Infarction", ASCP/CAP, Fall Proceedings, Abstract (1984).

Medeiros, L. J. et al, "Quantification of CK-MB by the Quick-MB and Tandem-E CK-MB Immunoassays: Comparison to Electrophoresis", *J. Clin. Immunoassay*, 8/3:152–156 (1985).

Clyne, C. A. et al, "Utility of the QuiCK-MB and Tandem CK-MB Immunoassays in Patients with Normal Total Serum CK and CK-MB>5%", *ACLPS Proceedings*, Abstract (1985).

Elser, R. C. et al, "Creatine Kinase B-Subunit Activity in Human Sera: Temporal Aspects of Its Sensitivity after Myocardial Infarction", *Clin. Chem.*, 27/1, 57–60 (1981).

Sax, S. et al, "Further Observations on the Incidence and Nature of Atypical Creatine Kinase Activity", *Clin. Chem.*, 25/4 535–540 (1979).

Griffiths, J. et al, "Creatine Kinase Isoenzyme MB in Myocardial Infarction: Methods Compared", *Clin. Chem.*, 23/3 (1977) 567–570.

Heal A. V. et al, "Clinical Assessment of Three Radio-Immunoassay Kits for the Diagnosis of Myocardial Infarction", *The Journal of Nuclear Medicine*, vol. 23, No. 5, p. P60.

DePuey, E. G. et al, "A New Creatine Kinase-MB Specific Radioassay to Diagnose Myocardial Infarction", *The Journal of Nuclear Medicine*, vol. 23, No. 5, p. P60.

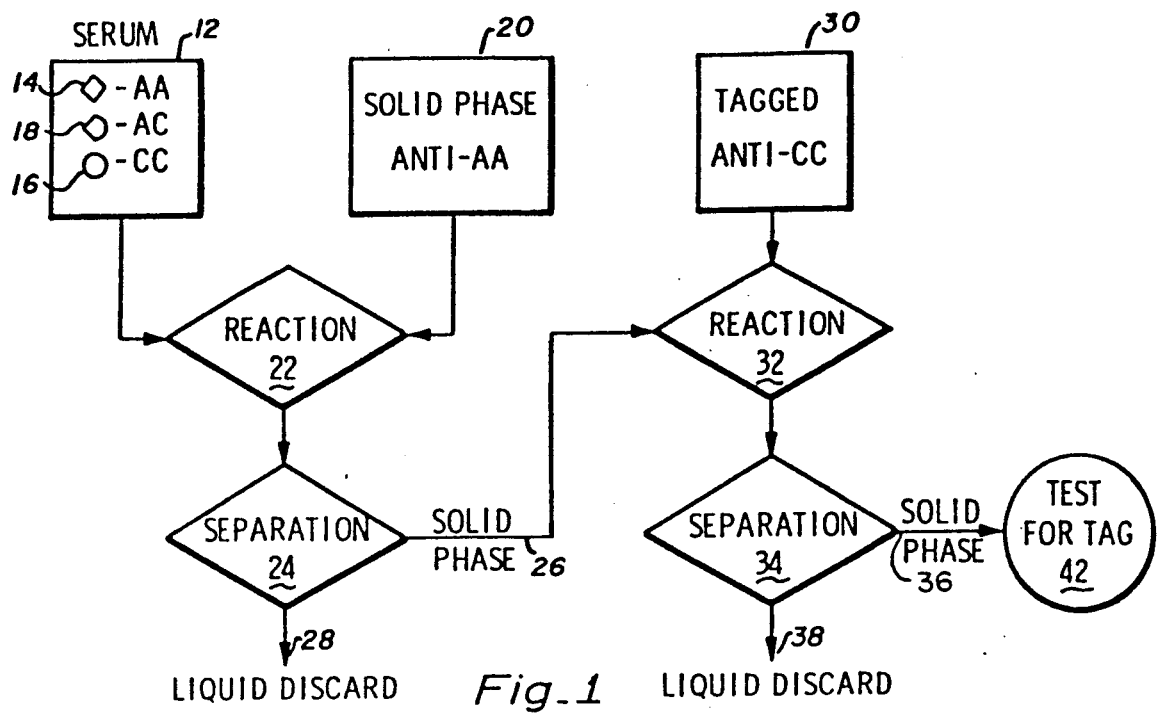
Fig_1
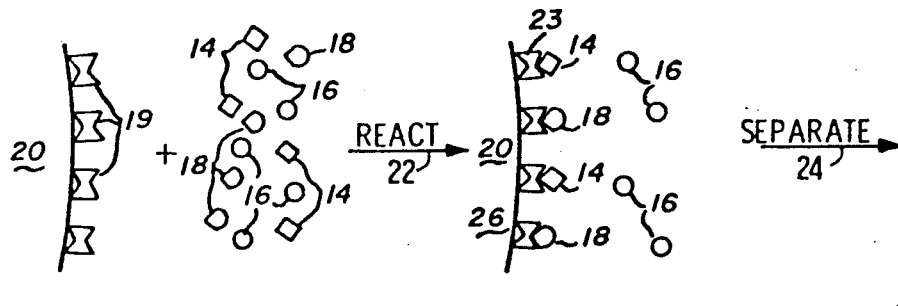
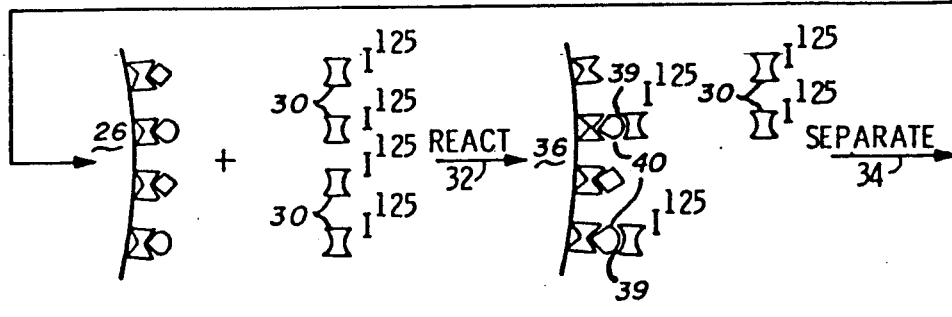
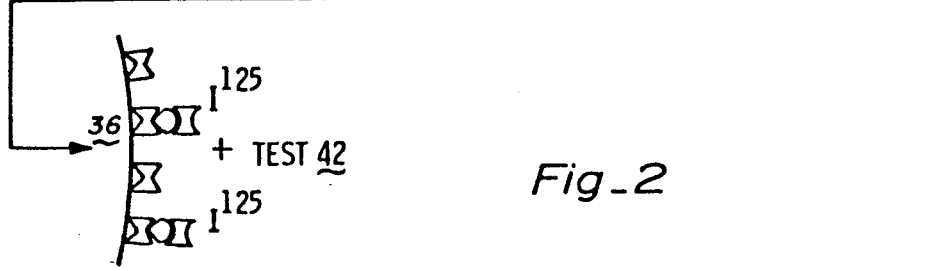
Fig_2

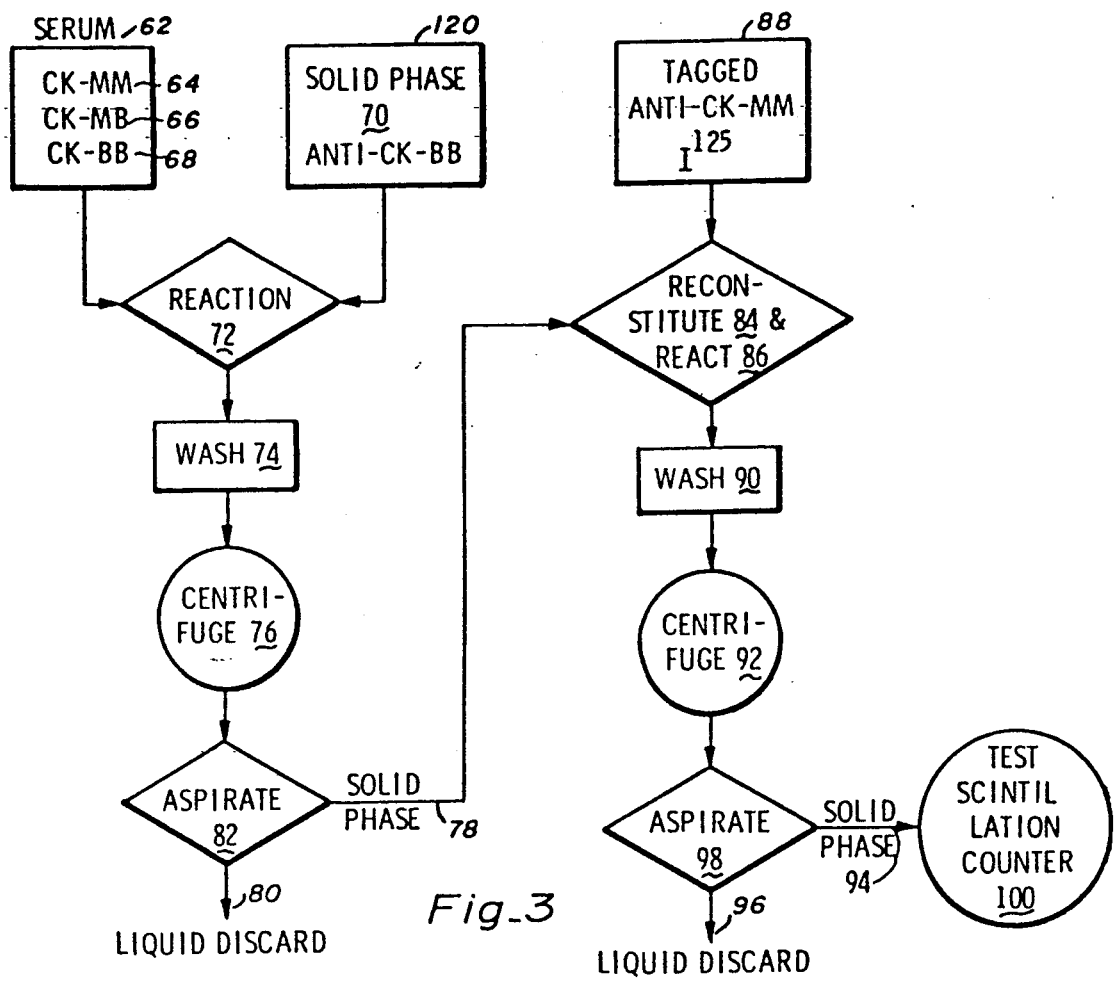
Fig_3
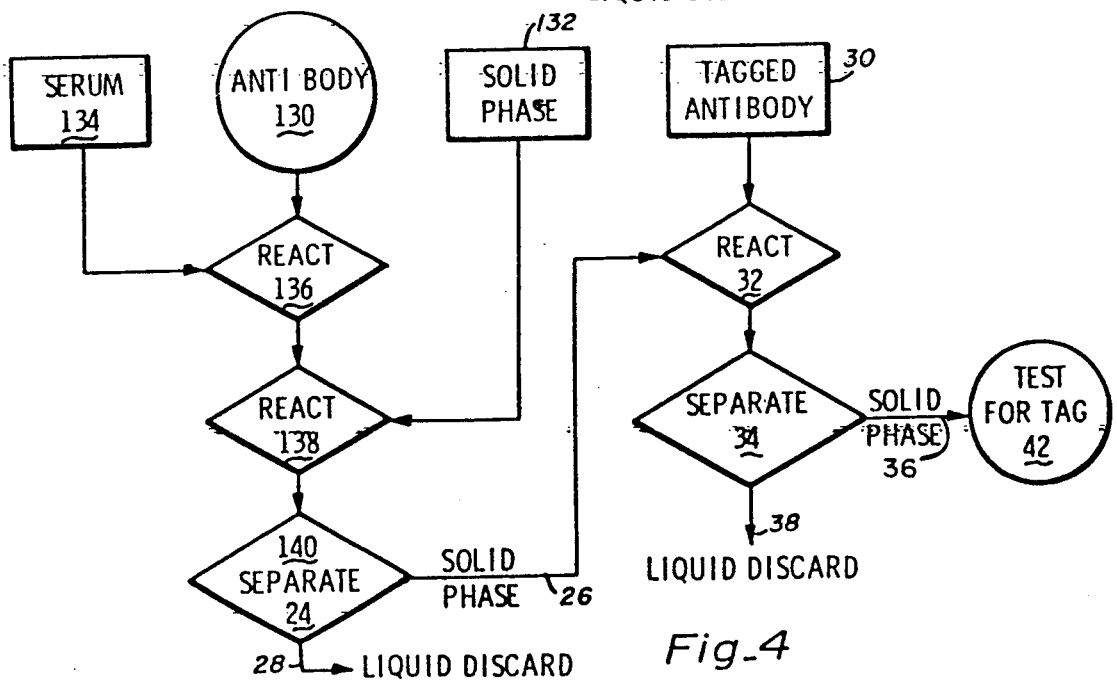
Fig_4

TWO SITE CROSS-REACTION IMMUNOMETRIC SANDWICH ASSAY METHOD

This is a continuation, of application Ser. No. 165,001 filed Jun. 30, 1980, now abandoned.

BACKGROUND OF THE INVENTION

1. Field of the Invention

The present invention relates generally to immunological assay techniques for determining the presence of an analyte in serum and more particularly to a two site cross-reaction immunoassay sandwich testing method which has particular application in the qualitative and quantitative determination of the level of the creatine phospho-kinase MB Isoenzyme (CK-MB) in human serum.

2. Description of the Prior Art

Conventional immunometric techniques depend upon the immunochemical reaction between a tagged antibody and the analyte to be assayed. Such antibodies are raised to specifically react with the particular analyte and may be tagged in a radioactive, fluorescent, chemiluminescent, enzymatic or other manner. However, many antibodies have cross-reactions with materials other than the specific analyte to be assayed whereupon the results of simple antibody-analyte tests become unreliable. To overcome this problem, sandwich type assay techniques have been developed which utilize two antibodies to sandwich the analyte therebetween.

Conventional sandwich techniques utilize three types of assays. In the first type, the undesired cross-reaction is reduced based on the observation that the undesirable cross-reactant would not react, at the same time, with antibodies specifically raised in two different animal species. Both of the antibodies are therefore raised against the specific analyte of interest, however they differ in that they are raised in different animal species, such as human beings and guinea pigs. Utilizing this sandwich technique, the undesirable effect of the unwanted cross-reactions of the first antibody is reduced through the utilization of the second antibody, whereby an accurate test for the analyte of interest is obtained. This type of sandwich assay technique is used in the detection of hepatitis.

The second type of sandwich assay is used when the serum contains, as metabolic by-products, fragments of the analyte to be measured. Two antibodies used for this assay are raised specifically against the analyte of interest. However, one antibody reacts specifically with one binding site the analyte while the second antibody reacts specifically with another binding site of the analyte. This prior art immunometric sandwich technique thus utilizes antibodies that are specifically raised against the specific analyte to be measured. The unwanted cross-reactions of the specific antibody with a fragment of the analyte of interest have caused researchers to develop this two site immunoassay sandwich technique which minimizes the effects of the unwanted cross-reactions from a fragment of the analyte.

The third sandwich technique uses the same specific antibody twice to detect the analyte of interest. In this technique an antibody which is specific to the analyte of interest is immobilized on a solid-phase and reacted with the analyte. All other interfering substances are removed before the analyte is reacted once again with the same antibody except that the antibody is now tagged for assay purposes.

As will be seen from the description of the preferred embodiment hereinbelow, the present invention differs from the prior art in that it specifically utilizes the previously avoided cross-reactive capabilities of two different antibodies to create a specific sandwich assay technique.

SUMMARY OF THE PRESENT INVENTION

It is therefore a primary objective of the present invention to provide an immunoassay technique which does not require the raising of an antibody which is specific to the analyte to be assayed.

It is another object of the present invention to provide a two site cross-reaction immunoassay sandwich technique which utilizes the cross-reactions of two different antibodies to provide a specific test for an analyte of interest.

It is a further object of the present invention to provide an immunoassay technique for determining the presence of CK-MB in human serum.

It is yet another object of the present invention to provide a two site cross-reaction immunoassay sandwich technique for the detection of CK-MB which utilizes the presently available antibodies for CK-MM and CK-BB.

The immunoassay technique of the present invention includes the selection of two different antibodies each of which is specific to a different analyte but each of which will cross-react with the analyte of interest. The first such antibody is affixed to a solid-phase and then reacted with the unknown sample. After reaction, the reactants are separated and the solid-phase portion thereof is retained. The second antibody, being tagged, is then reacted with the retained solid-phase portion. After reaction, the reactants are separated and the solid-phase portion is tested for the presence of the tag. Calibration tests are conducted concurrently with known amounts of the analyte of interest. The results of the test for the unknown can be compared therewith to provide a qualitative and quantitative determination of the presence of the analyte of interest.

With particular regard to the detection of CK-MB the immunoassay technique of the present invention includes reacting the unknown human serum with CK-BB antibody which is affixed to a solid-phase. After the reaction is complete, the reactants are washed, centrifuged and the liquid portion thereof is aspirated. The solid-phase portion, having been retained, is then reconstituted in solution containing tagged CK-MM antibody and reacted therewith. Upon completion of the reaction, the reactants are washed and centrifuged and the liquid portion is aspirated. The retained solid-phase portion is now tested for the presence of the tag. Calibration tests are also conducted utilizing serum having known amounts of CK-MB to provide a background with which to determine the quantity of CK-MB in the unknown sample.

A primary advantage of the present invention is that an antibody that is specific to the analyte of interest need not be created in order to provide an immunological assay test for the analyte. All that is required is that there be found two different antibodies which mutually cross-react only with the analyte. The technique is very useful for those analytes which are unstable and hence cannot be practically used to make antibodies. It is also very useful when it is extremely difficult to purify the analyte, as it is the case with cancer antigens.

It is another advantage of the present invention, as applied to the testing for CK-MB, that it utilizes the antibodies to CK-MM and CK-BB which are commercially available and inexpensive.

It is a further advantage of the present invention, as applied to the testing for CK-MB, that the test may be performed rapidly and with greater accuracy than test procedures presently available.

These and other objects and advantages of the present invention will no doubt become apparent to those of ordinary skill in the art after having read the following detailed description of the preferred embodiments which are illustrated in the several figures of the drawing.

IN THE DRAWING

FIG. 1 is a flow chart depicting the two site cross-reaction immunometric sandwich assay method of the present invention;

FIG. 2 is a schematic diagram of the assay method of the present invention;

FIG. 3 is a flow chart depicting the assay method of the present invention as applied to the detection of CK-MB;

FIG. 4 is a flow chart depicting an alternative embodiment of the assay method of the present invention.

DETAILED DESCRIPTION OF THE PREFERRED EMBODIMENT

In standard sandwich assay techniques, two antibodies are utilized, each of which is raised against the specific analyte of interest. The utilization of the two specific antibodies gives a very high probability of detection of the analyte and a very low probability of error due to unwanted cross-reactants. However, such sandwich techniques cannot be utilized where an antibody that is specific to the analyte of interest has not been created or isolated. The present invention has application in just such a circumstance.

Where it has proven difficult to create and/or isolate a specific antibody for the detection of an analyte of interest, it may well be the case that known antibodies exist which, while specific to other analytes, will mutually cross-react only with the analyte of interest. Where two such antibodies exist, each being specific to a different analyte but each being capable of cross-reacting with the analyte of interest and there being no other analyte to which they both will cross-react, the test procedure of the present invention will permit detection and assay of the mutually cross-reacting analyte of interest. It will be seen that just such a situation exists with regard to the immunological assay for creatine phospho-kinase-MB (CK-MB).

As depicted in FIGS. 1 and 2, the general test procedure of the present invention is performed on a serum sample 12 containing three related analytes which are schematically depicted as a diamond shaped analyte 14, hereinafter referred to as AA, a circular shaped analyte 16, hereinafter referred to as CC, and a hybrid analyte 18 of the two other analytes, shown as having both a partial diamond shape and a partial circular shape, hereinafter referred to as AC. It will be assumed that antibodies exist which are specific to AA, hereinafter referred to as anti-AA, and to CC, hereinafter referred to as anti-CC, but that the antibody to AC is unstable and therefore non-existant for testing purposes. However, both anti-AA and anti-CC will cross-react with AC due to the similarity of molecular structure of the A and C binding sites of the AC molecule to the AA and CC molecules.

In an initial procedure, which is performed prior to or concurrent with the first reaction step described hereinbelow, anti-AA 19 is affixed to a solid-phase 20 using a standard immunological procedure therefor. Also, in a separate immunological procedure performed prior to the instant test, anti-CC is tagged for later detection. Procedures for tagging antibodies are well known and radioactive, fluorescent, chemiluminescent, enzymatic or other types of tags are appropriate for this test procedure.

In the first reaction step 22, the serum 12 is combined with the solid-phase anti-AA 20 and reacted therewith for an appropriate time and temperature. The time and temperature will vary with the particular antibodies and analytes involved in the test procedure, as well as the concentrations thereof. In the reaction the solid phase anti-AA 20 immunochemically binds 23 with the AA 14 and removes all of the AA from the serum as it is specific to that analyte. Additionally, because the anti-AA 19 will cross-react and immunochemically bind with the a binding site of AC 18, all of the AC is also removed from the serum.

In the next step of the test procedure, the reactants are separated 24, the solid-phase products 26 being retained and the liquid 28 being discarded. Standard separation procedures, such as centrifugation and aspiration, are utilized. It is to be noted that the discarded liquid 28 contains all of the CC analyte.

The retained solid-phase 26 is now reacted 32 with the tagged anti-CC 30. The reaction 32 is allowed to continue for an appropriate time at an appropriate temperature. Again, the time and temperature will vary with the particular antibodies and analytes involved in the test procedure, as well as the concentrations thereof.

Thereafter, a standard separation step 34, is performed wherein the solid-phase 36 is retained and the liquid 38 is discarded. As is schematically shown in FIG. 2, the tagged anti-CC 30 can only cross-react and immunochemically bind 39 with the C binding site of those molecules of AC which have previously cross-reacted with the solid phase anti-AA 26; all of the CC having been discarded in the liquid portion 28 of the first separation step 24.

It is now seen that the remaining solid-phase 36 contains a tagged sandwich of molecules 40 in which the AC (the analyte of interest) is sandwiched between two antibodies, neither of which is specific to that analyte but each of which will cross-react with it.

The solid-phase 36 may now be tested 42 for the tag, which test will give an indication of the presence of the analyte of interest.

Calibration tests utilizing known amounts of the analyte of interest and the above-described test procedure are conducted simultaneously to create a calibration curve against which to gauge the results of the test for the unknown sample. Further tests utilizing known dilutions of the unknown sample and the above-described test procedure may also be performed to obtain test results which fall on sensitive portions of the calibration curve.

A specific application of the above-described test procedure for use in the detection of CK-MB antigen in human serum can now be described.

As is well known, human serum contains three creatine phospho-kinase isoenzymes; creatine phospho-kinase-MM (a skeletal tissue extract, hereinafter referred to as CK-MM), creatine phospho-kinase-BB (a brain tissue extract, hereinafter referred to as CK-BB) and creatine phospho-kinase-MB (a heart tissue extract, hereinafter referred to as CK-MB) which is a hybrid form of CK-MM and CK-BB. A great deal of research has been conducted to develop a test for CK-MB in that its presence is a specific indication of myocardial infarction or similar heart disturbances. However, testing for CK-MB by various methods has proved to be quite difficult as its properties are quite similar to CK-MM and CK-BB, the presence of which can significantly mask small amounts of CK-MB. With particular regard to immunometric assay techniques for the detection of CK-MB, these have been made difficult by the present inability of researchers to prepare and develop stable antibody which is specific to the CK-MB (hereinafter referred to as anti-CK-MB), and no such anti-CK-MB is commercially available at this time. However, it is known that the antibodies to both CK-MM and CK-BB (hereinafter referred to as anti-CK-MM and anti-CK-BB respectively) will cross-react with CK-MB, in addition to their having specific reactions with CK-MM and CK-BB respectively. The test procedure described hereinabove is therefore applicable to the detection of CK-MB in accordance with the following description.

Prior to the actual assay of serum, anti-CK-BB is affixed to a solid phase as is described hereinbelow. However, as is also described hereinbelow an alternative embodiment of the above-described test procedure may be performed in which this step is not performed. Additionally, prior to assay the anti-CK-MM must be tagged, such as is described hereinbelow by the utilization of radio-active iodine ($^{125}$I).

Anti-CK-BB (rabbit) for affixation to a solid-phase is commercially available from many sources. The solid-phase selected for linkage with the anti-CK-BB was Bio-Rad Immuno-Beads (catalog no. 170-5602) although other solid phases could be utilized such as latex beads or cellulose beads or a membrane strip. Bio-Rad Immuno-Beads are polyacrylamide beads having a diameter of approximately 10 $\mu$(microns) and which are designed for use as a solid phase in immunoassay testing. Following the procedure recommended by the manufacturer, the beads were first covalently linked to goat anti-rabbit IgG. 50 mg of beads were then suspended in 25 to 50 ml of PBS containing 10% calf serum, although other proteins could be used to minimize non-specific binding. Thereafter, the beads were washed with PBS buffer (pH approximately 7.4, 0.02M $PO_4$, 0.15M NaCl). The beads were then slurried in 25 ml PBS containing 1% BSA. Approximately 100 $\mu$l of anti-CK-BB was then reacted with the beads to link the anti-CK-BB to the beads. The antibody coated beads were then washed and separated from unreacted anti-CK-BB with PBS buffer. The anti-CK-BB coated beads were then ready for utilization in the test procedure.

Prior to testing, the anti-CK-MM is iodinated with radioactive iodine (125$i$) to serve as a tag for the detection of CK-MB. Such tagging procedures are well known, see FRAKER, T. and SPECK, J., *Bio-chemical and Bio-physical Research Commission*, volume 80, no. 4, February, 1978. In the procedure, 100 $\mu$g of anti-CK-MM (goat) was dissolved in 100 $\mu$l of water. Sixteen $\mu$l of this solution, to be used for tagging, was combined with 20 $\mu$l (0.25M $PO_4$) PBS buffer (pH, 7.5) in a reaction vial. 480 microcurie of NaI$^{125}$ was added to this buffer. This was followed by 10 $\mu$l (3.5 mg/ml in 0.05 phosphate buffer) of chloramine-T solution. This was mixed for 60 seconds followed by 10 $\mu$l of sodium metabisulfite solution (3.5 mg/ml 0.05 phosphate buffer). The reaction mixture was fractionated over a Sephadex G-50 column (washed and treated with goat serum), fractions numbered 18-23 were collected and pooled. The fraction pool was purified over a Dowex 1×8 column and collected. This material was diluted to achieve an appropriate activity level.

Utilizing the previously prepared solid-phase anti-CK-BB and radioiodinated anti-CK-MM, the test procedure for CK-MB is performed as depicted in FIG. 3.

Human serum 62 containing the isoenzymes CK-MM 64, CK-MB 66 and CK-BB 68 is reacted 72 with the anti-CK-BB coated Immuno-Beads 70. The reaction time and reaction temperature being parameters which may be varied depending upon the concentration of the serum and the strength of the anti-CK-BB on the Immuno-Beads. As is demonstrated in Example II hereinbelow, these variables may be adjusted such that good test results are obtainable utilizing room temperature and a reaction time of one hour.

Following the reaction phase 72, it is necessary to separate the liquid from the beads. To accomplish this, approximately 2 ml of additional PBS buffer is added to the reactants as a wash 74. The reactants are then centrifuged 76 to achieve a button-like precipitate 78. Centrifuging at room temperature for approximately ten minutes at a speed of approximately 2000 rpm has been found to yield good results.

Having achieved a button-like precipitate 78 at the bottom of the test vial the liquid 80 therein is aspirated 82 and discarded, and the precipitate 78 is retained for the second phase of the test procedure.

It is noted that the anti-CK-BB coated beads will have reacted with, and therefore removed from solution, all of the CK-BB and CK-MB antigens. As the CK-MM antigen does not react with the anti-CK-BB, the CK-MM remains in solution and is discarded with the aspirated waste water 80.

The second reaction phase 86 of the test procedure is now initiated by the addition of the radioiodinated anti-CK-MM 88 to the precipitate. The reactants are vibrated or vortexed to reconstitute 84 the precipitate into the reaction. The reaction time and reaction temperature are parameters which may be varied in accordance with the concentrations of the reactants. As is demonstrated in Example II good test results may be obtained with the utilization of room temperature and a reaction time of approximately 1 hour.

After reaction 86, a second separation is performed in the same manner as the prior separation. That is, approximately 2 ml of PBS wash buffer 90 containing 0.1% Tween 20 is added to the reactants and the reactants are centrifuged 92 at room temperature for an approximate time of ten minutes at an approximate speed of 2000 rpm to yield a button-like precipitate 94 at the bottom of the test vial. The liquid 96 in the test vial is then aspirated 98 and discarded in an appropriate manner, in that it contains excess radioactive anti-CK-MM. The button-like precipitate 94 is then tested 100 with a scintillation detector to indicate the presence of radiation as a possible indication in the test serum.

It is important to note that as all of the CK-MM was aspirated 82 and discarded in the liquid 80, there was no CK-MM present in the second reaction 86 with which the anti-CK-MM could specifically react. The only reaction possible for the anti-CK-MM was then to cross-react with the CK-MB that was bound to the beads by virtue of its cross-reaction with the anti-CK-BB.

As with all radioimmunoassay techniques, it is necessary to perform concurrent calibration tests with known amounts of CK-MB to form a calibration curve against which to compare the results of the unknown test. It is noted that there will always be some radiation from a zero level CK-MB sample due to the attachment of the radioiodinated anti-CK-MM to the walls of the test vial and remaining in any moisture within the precipitate 94 after centrifuging 92. Thus, there will be radiation from a zero level CK-MB sample and it is the increase in radiation over the zero level of radiation that provides an indication of the presence of CK-MB in the test sample.

Furthermore, it is well known in radioimmunoassay testing that the increase in radioactivity does not vary linearly with increasing amounts of analyte in the test serum. The variation of radiation with concentration of analyte depends upon many variables, such as quantity of antibody, dilution of antibody, antibody-analyte ratio and others. The standard test procedure which is utilized to overcome this testing impediment is to perform a series of tests with varying known dilutions of the unknown test serum. A series of results are then obtained, one or more of which will lie on a sensitive portion of the calibration curve to give an accurate indication of the level of analyte in the sample. The Examples I, II and IV given hereinbelow demonstrate the utilization of this procedure.

As would be obvious to those skilled in the art, alternative solid-phase materials such as a membrane filter could be utilized instead of the Immuno-Beads. In exploring this alternative, a membrane 120 was created utilizing Whatman no. 1 filter paper which was oxidized using the periodate technique described by Ferrung, B., Maiolini, R., and Masseyeff, R., *Journal of Immunological Methods*, Volume 25, page 49, 1979. Strips of the membrane were soaked in goat anti-rabbit $I_gG$ solution and utilized in much the same manner as the immuno-beads are used in the test. The use of membrane as the solid-phase eliminates the need to centrifuge, and the separation steps become the simple washing of the membrane to remove excess immunoreagents. Results using a membrane solid-phase are presented in Example VI hereinbelow.

A variation on the above described test procedure, see FIG. 4, may be conducted in the following manner. Rather than affixing the first antibody 130 to a solid-phase 132, the first antibody 130 is added 136 directly to the unknown serum 134. Thereafter, the solid-phase 132, which has not been coated with the first antibody 130, but which is prepared for coating as described hereinabove, is added 138 to the reactants. The reaction 138 is then permitted to proceed in the manner described hereinabove and the remaining steps of the test procedure are conducted as previously described following reaction 72 of FIG. 3. It is found that sufficient amounts of the solid-phase antibody-antigen complex attach to the beads 132 to give adequate test results. Examples IV and V presented hereinbelow are specific examples of the results achieved utilizing this variation of the test procedure.

The following examples demonstrate the instant testing method using several combinations of test conditions.

EXAMPLE I

This experiment was carried out with anti-CK-BB coated immuno-beads. 100 μl of sample was mixed with 200 μl of beads. After overnight incubation at room temperature, 0.5 ml PBS buffer with 10% calf serum was added to the test tube. The beads were separated by centrifugation. They were then reacted for 5 hours at room temperature with radioiodinated anti-CK-MM. After incubation, beads were washed with 1 ml PBS buffer with 10% calf serum. The beads were then centrifuged and counted.

Results

Normal human serum count (NHS)—1090 counts per min.

| Calibrators (100 μl per test) | Ratio $\frac{\text{Sample Counts}}{\text{NHS COUNTS}}$ |
|---|---|
| E. 1 μg/ml of CK-MB powder in serum | 1.17 |
| D. 10 μg/ml of CK-MB powder in serum | 3.20 |
| C. 50 μg/ml of CK-MB powder in serum | 5.71 |
| B. 100 μg/ml of CK-MB powder in serum | 6.65 |

The calibrator samples were made by dissolving a powder containing 6–8% CK-MB in normal human serum at various dilutions.

| Patient Samples (known to have high level of CK-MB) | | |
|---|---|---|
| High level | 10 μl | 3.66 |
| | 25 μl | 7.44 |
| | 50 μl | 12.1 |
| | 100 μl | 14.9 |

As is seen, a good response curve was obtained with CK-MB calibrators, and patient sample, which was identified as having high CK-MB content by other techniques, could be measured utilizing four dilutions to assure a reading level that was correlatable on the calibration curve.

EXAMPLE II

This example shows effect of reducing incubation time and varying the amount of beads to 200 μl and 500 μl. The wash buffer used was 2 ml PBS with 5% calf serum and was added before each centrifugation. The incubation time was one hour for each of the reactions at room temperature. Other test conditions were identical to those of Example I.

| | | Results | |
|---|---|---|---|
| | | 200 μl Beads | 500 μl Beads |
| | | Counts (cpm) | |
| | NHS | 913 | 1475 |
| | | Ratio $\frac{\text{Sample Counts}}{\text{NHS COUNTS}}$ | |
| High | 50 μl | 2.35 | 2.85 |
| | 100 μl | 3.31 | 3.77 |
| Calibrater | 50 μg/ml | 2.24 | 3.25 |
| | 100 μg/ml | 2.8 | 4.50 |

The ratios obtained, although significantly lower than the overnight incubation, were still quite acceptable. The effect of reduction in incubation time thus can be compensated by increasing the amount of beads.

EXAMPLE III

The method described in Example II was used with 200 μl of beads and an incubation time of 1.5 hours for each reaction. The tracer used in this experiment had higher non-specific binding. Several serial samples of a patient just admitted to a hospital for a myocardial infarct were tested.

| Sample | Count |
|---|---|
| NHS | 3835 counts per minute |
| Calibrators | Ratio $\frac{\text{Sample Counts}}{\text{NHS COUNTS}}$ |
| 50 μg/ml | 2.2 |
| 100 μg/ml | 2.7 |
| PATIENT A: | |
| 11 A.M. | 2.24 |
| 12 NOON | 2.75 |
| 1 P.M. | 3.00 |
| 4 P.M. | 3.15 |
| 8 P.M. | 3.54 |
| NORMAL PATIENTS: | |
| B | .94 |
| C | 1.06 |
| D | .99 |

The rising levels of CK-MB shown in this Example demonstrate the well known increase in CK-MB levels in the patient following a myocardial infarct or similar incident.

EXAMPLE IV

In this example, polyacrylamide beads were used as a precipitating antibody. In the first step, diluted (1:30) anti-CK-BB was added to the sample. Bio-Rad Immuno-beads were suspended in 50 ml PBS buffer with 1% BSA, 500 μl of these beads being comparable in number of beads to 250 μl of beads used in previous examples. These beads were not precoated with anti-CK-BB. After a one hour incubation period, the reactants were centrifuged and aspirated. A second incubation of one hour was carried out in the normal manner. Thereafter, 2 ml of PBS buffer with 1% BSA and 1% Tween was added and reactants were centrifuged, aspirated and the solid-phase counted. The results were as follows:

| Sample | Count |
|---|---|
| NHS | 2076 |
| Calibraters | Ratio $\frac{\text{Sample Counts}}{\text{NHS COUNTS}}$ |
| 50 μg/ml | 3.1 |
| 100 μg/ml | 4.2 |

The above sample contained roughly 5 mIU/ml and 10 mIU/ml CK-MB which is roughly the limit of normal range.

EXAMPLE V

Negative samples were run using the method discussed in Example IV.

| RESULTS | | | |
|---|---|---|---|
| | SAMPLE | COUNTS | Standard Deviation |
| RUN 1 | NHS | 2015 | |
| | 13 negative samples | 2260 | 305 |
| RUN 2 | NHS, 16 times | 2017 | 199 |
| | 12 negative samples with high total CK Calibrater | 2172 | 300 |
| | 50 μg/ml | 4281 | |
| | 100 μg/ml | 5936 | |

Thus negative samples, even those with high total CK levels, would all be well under the 50 μg/ml calibrator sample and are seen to be quite close to the NHS samples.

EXAMPLE VI

The use of a membrane as a solid-phase is demonstrated by using anti-CK-BB immobilized on Whatman no. 1 filter paper as described hereinabove.

The antibody coated membrane (1"×1") was placed in a mixture of sample and 2 ml PBS 5% BSA buffer. After a first incubation of 1 hour, the liquid was aspirated and the membrane was thoroughly washed. Radioiodinated anti-CK-MM was added. After a second incubation of one hour the liquid was aspirated. The membrane was washed thoroughly and transferred to another tube. The results were as follows:

| RESULTS | |
|---|---|
| Sample | |
| NHS | 967 counts per minmute |
| Calibrator | Ratio $\frac{\text{Sample Counts}}{\text{NHS COUNTS}}$ |
| 400 μg/ml | 3.3 |
| 100 μg/ml | 1.9 |

Thus, a membrane solid-phase is seen to produce cognizble results although they are not as pronounced as were the results utilizing the beads as the solid-phase.

It can therefore be seen that the present invention derives its uniqueness from the utilization of the cross-reactive capabilities of the antibodies that are selected for use. This is in contradistinction to standard immunological assay techniques in which the cross-reactive capabilities of the antibodies are minimized or avoided through the use of multiple antibodies which are each specific to the analyte of interest. Utilization of the instant test technique for the detection of CK-MB in human serum provides a rapid and effective means for the detection and identification of myocardial infarcts and similar heart disturbances in patients immediately following their occurance.

Whereas the preferred embodiment of the present invention has been described above, it is contemplated that other alterations and modifications may become apparent to those skilled in the art after having read the above disclosure. It is therefore intended that the appended claims be interpreted as covering all such alterations and modifications as fall within the true spirit and scope of the invention.

What is claimed is:

1. A two-site immunometric sandwich assay method for the detection and measurement of an analyte of interest in a test sample, said analyte of interest having at least two immunochemically differing binding sites, comprising:
- (a) combining a first antibody, raised against a material other than said analyte of interest and capable of cross-reacting with one of said at least two binding sites of said analyte of interest, with a test sample suspected of containing said analyte of interest and a solid material capable of specifically binding to said first antibody, to form a first reaction medium, and simultaneously reacting the components of said first reaction medium to form a bound complex of said solid material to said first antibody, which first antibody is further bound with any other reactants in said test sample which are capable of immunochemically binding to said first antibody;
- (b) separating the solid phase from the liquid phase of the reaction medium;
- (c) reacting said solid phase, in a second reaction medium, with a second antibody, said second antibody having been raised against a material other than said analyte of interest and being capable of cross-reacting with another of said at least two binding sites of said analyte of interest, and said second antibody being tagged with a means for making said tagged antibody detectable;
- (d) separating the solid phase portion of said second reaction medium from the liquid phase portion thereof; and
- (e) testing said solid portion to detect the quantity of said second antibody therein as an indication of the presence of said analyte of interest, wherein said analyte of interest and said materials other than said analyte of interest against which said first and second antibodies have been raised are three different but related molecules, wherein said other materials may be representationally depicted as AA and CC, wherein A and C are binding sites on the materials, and said analyte of interest is a hybrid AC of the other two materials, and wherein the molecular structure of the A binding sites in AA and AC, and the C binding sites in CC and AC are sufficiently similar to permit cross-reaction therebetween by antibodies raised against either material, said first and second antibodies being selected such that they will not both cross-react with any analyte in the test sample other than said analyte of interest.

2. An assay method as recited in claim 1, wherein said solid material is selected from the group consisting of polyacrylamide beads, latex beads, cellulose beads and membrane strip.

3. An assay method as recited in claim 1, wherein said tag is radioactive iodine $^{125}I$.

4. An assay method as recited in claim 1, wherein said tag is an enzymatic tag.

5. An assay method as recited in claim 1, wherein said separating steps are accomplished by centrifuging the media to precipitate said solid phase portion thereof and by aspirating to remove said liquid phase portion therefrom.

6. An assay method in accordance with claim 1, further including the steps of repeating said steps (a) to (e) with several known dilutions of said analyte of interest to obtain a calibration curve and plotting the amount of analyte of interest against the amount of detected second antibody, whereby the amount of analyte of interest in an unknown sample can be quantified by comparison to said calibration curve.

7. An assay method in accordance with claim 1, wherein said analyte of interest is creatine phosphokinase-MB (CK-MB), said first antibody has been specifically raised against creatine phospho-kinase-BB (CK-BB) and said second antibody has been specifically raised against creatine phospho-kinase-MM (CK-MM).

8. An assay method in accordance with claim 7, wherein said test sample suspected of containing said analyte of interest is human serum.

9. An assay method as recited in claim 7, wherein said solid material is a material selected from the group consisting of polyacrylamide beads, latex beads, cellulose beads and membrane strip.

10. An assay method as recited in claim 7, wherein said tag is radioactive iodine $^{125}I$.

11. An assay method as recited in claim 7, wherein said tag is an enzymatic tag.

* * * * *